United States Patent
Breviere et al.

(10) Patent No.: US 7,032,444 B2
(45) Date of Patent: Apr. 25, 2006

(54) MODULE FOR EXTRACTING GAS FROM AN UNDERGROUND LIQUID AND INSTALLATION EQUIPPED THEREWITH

(75) Inventors: Jérôme Breviere, Taverny (FR); Jean-François Evrard, Fontenay Sous Bois (FR)

(73) Assignee: Geoservices, Le Blanc-Mesnil (FR)

( * ) Notice: Subject to any disclaimer, the term of this patent is extended or adjusted under 35 U.S.C. 154(b) by 76 days.

(21) Appl. No.: 10/488,885

(22) PCT Filed: Sep. 23, 2002

(86) PCT No.: PCT/FR02/03243

§ 371 (c)(1),
(2), (4) Date: Mar. 25, 2004

(87) PCT Pub. No.: WO03/027641

PCT Pub. Date: Apr. 3, 2003

(65) Prior Publication Data

US 2004/0231407 A1   Nov. 25, 2004

(30) Foreign Application Priority Data

Sep. 25, 2001 (FR) .................................. 01 12334

(51) Int. Cl.
*G01N 1/10* (2006.01)
*E21B 49/08* (2006.01)
(52) U.S. Cl. .................. 73/152.23; 73/152.18; 73/863.71; 73/863.81; 73/864.81; 96/217; 96/413
(58) Field of Classification Search ............. 73/19.01, 73/19.03, 19.09, 19.1, 19.11, 19.12, 152.01–152.04, 73/152.06, 152.08, 152.18, 152.23, 863.71, 73/863.81, 864.81; 96/217, 413; 436/28–30
See application file for complete search history.

(56) References Cited

U.S. PATENT DOCUMENTS

| | | | |
|---|---|---|---|
| 2,341,169 A | | 2/1944 | Wilson et al. |
| 2,514,690 A | * | 7/1950 | Bliss et al. ................. 73/19.09 |
| 3,240,068 A | * | 3/1966 | Horeth et al. ............. 73/863.12 |
| 3,418,841 A | * | 12/1968 | Issenmann .................. 73/19.01 |
| 4,326,863 A | * | 4/1982 | Day et al. ..................... 96/182 |
| 4,559,808 A | * | 12/1985 | Sturman .................... 73/19.01 |
| 4,635,735 A | * | 1/1987 | Crownover .................. 175/48 |
| 4,887,464 A | * | 12/1989 | Tannenbaum et al. ... 73/152.04 |
| 4,904,603 A | * | 2/1990 | Jones et al. .................. 436/25 |
| 5,090,256 A | | 2/1992 | Issenmann |
| 5,191,786 A | * | 3/1993 | Baughman et al. ........ 73/64.45 |
| 5,199,509 A | * | 4/1993 | Wright et al. ................ 175/50 |

(Continued)

FOREIGN PATENT DOCUMENTS

EP   0370548   5/1990

(Continued)

*Primary Examiner*—Hezron Williams
*Assistant Examiner*—David A. Rogers
(74) *Attorney, Agent, or Firm*—Wenderoth, Lind & Ponack, L.L.P.

(57) ABSTRACT

This invention concerns a module for extracting samples in gas phase of compounds present in an underground working liquid, the extractor module including a receptacle for the liquid, associated with a device for stirring the liquid, a liquid inlet duct, a liquid evacuation duct, an auxiliary gas admission duct, and an outlet duct for delivering auxiliary gas and gas extracted from the liquid. The auxiliary gas admission duct and the evacuation duct include a common segment, for preventing the auxiliary gas from passing is provided in the evacuation duct downstream from the common segment in the liquid-passing direction.

25 Claims, 6 Drawing Sheets

U.S. PATENT DOCUMENTS

| | | | |
|---|---|---|---|
| 5,447,052 A * | 9/1995 | Delaune et al. | 73/19.09 |
| 5,646,336 A * | 7/1997 | Thompson et al. | 73/61.43 |
| 5,648,603 A * | 7/1997 | Hanson | 73/152.02 |
| 5,734,089 A * | 3/1998 | Thompson et al. | 73/19.12 |
| 5,777,214 A * | 7/1998 | Thompson et al. | 73/61.59 |
| 6,389,878 B1 * | 5/2002 | Zamfes | 73/19.09 |
| 6,436,710 B1 * | 8/2002 | Sivavec et al. | 436/39 |
| 6,443,001 B1 * | 9/2002 | Duriez et al. | 73/152.19 |
| 6,485,688 B1 * | 11/2002 | Sivavec et al. | 422/83 |
| 6,520,034 B1 * | 2/2003 | Masquelier et al. | 73/863.21 |

FOREIGN PATENT DOCUMENTS

| | | |
|---|---|---|
| EP | 0555965 A2 | 8/1993 |
| FR | 2799790 | 4/2001 |

* cited by examiner

MODULE FOR EXTRACTING GAS FROM AN UNDERGROUND LIQUID AND INSTALLATION EQUIPPED THEREWITH

BACKGROUND OF THE INVENTION

The invention relates to a module for extracting samples in gas phase of compounds present in an underground working liquid. The invention also relates to an installation for analyzing gas samples and including such an extractor module.

U.S. Pat. No. 5,090,256 provides for an installation of this kind, in which the extractor module receives a drilling liquid from a pump fed from a head for taking liquid samples. The extractor module stirs the liquid to release the gases that are to be found therein. The released gases are collected from the extractor module for subsequent analysis in a device located downstream.

That extractor module presents the drawback of being capable of extracting only part of the gases contained in the liquid, and in particular it does not enable heavy hydrocarbons of C5 to C8 order to be extracted.

French patent document FR-A-2 799 790 provides a receptacle for extracting gas from liquid fed by a pump and evacuated by a delivery line. A pipe connects the receptacle to means for analyzing and measuring the extracted gas, and an inlet for a gas, air or inert gas, admits gas into the receptacle in order to adjust the gas entry flow rate.

That receptacle for extracting gas, and the installation in which it is provided, also present a certain number of drawbacks.

In practice, the gas inlet often becomes clogged, contrary to the looked-for effect.

It is necessary to cause a large volume of liquid to flow through the receptacle in order to extract a quantity of gas that is sufficient for analysis.

Finally, the large volume of liquid in the receptacle requires heater means to deliver a large amount of heat, consequently consuming a large amount of energy, whereas little electrical energy is available in the vicinity of the extractor module.

The invention seeks to obtain an extractor module and an installation including the extractor module that mitigate the drawbacks of the prior art.

SUMMARY OF THE INVENTION

To this end, a first aspect of the invention provides an extractor module for extracting gas samples of compounds present in an underground working liquid, the extractor module comprising:

a receptacle for said liquid, associated with means for stirring the liquid in the receptacle in order to extract the compounds in the gas phase from the liquid, and connected to the receptacle when it is operating to extract gas:

at least one liquid inlet duct for admitting liquid into the receptacle;

at least one liquid evacuation duct for evacuating liquid from the receptacle;

at least one auxiliary gas admission duct for admitting auxiliary gas into the receptacle; and at least one outlet duct for delivering auxiliary gas and gas extracted from the liquid, for connection to gas reception.

The module is characterized in that the auxiliary gas admission duct and the liquid evacuation duct include at least one common segment for passing the liquid and the auxiliary gas. Means for preventing the auxiliary gas from passing is provided in the liquid evacuation duct downstream from the common segment in the liquid-passing direction.

By means of the invention, the efficiency with which gas is extracted from the volume of liquid contained in the receptacle is increased, both in terms of quantity and in terms of quality. It thus becomes possible to extract gaseous or liquid hydrocarbon compounds from the liquid in the range methane to octane, including aromatic compounds such as benzene-toluene-ethylbenzene-xylenes (BTEX) together with other gases such as hydrogen sulfide.

The inventors have also discovered that there could exist a dead volume of gas extracted from the liquid that stagnates in the receptacle, only a small quantity of which could be taken for sending to the means for analyzing the extracted gases. By means of the invention, this dead volume in the receptacle is decreased and the auxiliary gas is given a large area of contact with the liquid, thus encouraging the extraction of gas. The increase in extraction efficiency makes it possible to dimension the extractor module in a manner that is much more suitable for the quantity of gas needed for analysis purposes, thus making it possible to reduce the dimensions of the extractor module for a given volume of analyzed gas. In addition, there is no longer any need to supply so much heat for heating the liquid since a smaller volume of liquid is to be heated. The extractor module and the installation are thus made more efficient and less expensive.

In an embodiment of the invention that serves to reduce the extent to which the materials contained in the liquid clog and settle in the auxiliary gas admission duct, the common segment communicates with the receptacle via a fluid-passing window for passing the auxiliary gas and the liquid, and having, in its bottom portion, at least one edge lying substantially in a plane. Naturally, this fluid-passing window can be provided in any liquid evacuation duct and is independent of other characteristics.

In an embodiment of the invention that is simple to implement, provision is made for the window to have a profile that is rectangular.

In order to prevent the auxiliary gas admission duct from being dirtied by the liquid, provision is made in an embodiment of the invention for the auxiliary gas admission duct to open out into the liquid evacuation duct at a portion thereof that is situated so as to be substantially sheltered from splashes of liquid coming from the receptacle.

In an embodiment of the invention, adapted to rotary stirring of the liquid, the stirring means comprises a rotary stirrer and the auxiliary gas admission duct opens out into the liquid evacuation duct at a portion situated further upstream than downstream in the direction of rotation of the rotary stirrer.

In an embodiment of the invention, the auxiliary gas admission duct opens out into the liquid evacuation duct in a portion lying at a distance from the receptacle.

In an embodiment of the invention that facilitates liquid flow in the receptacle, the liquid evacuation duct slopes downwards relative to the receptacle.

An embodiment of the invention makes provision for the auxiliary gas admission duct to present both a segment for coupling to the liquid evacuation duct and an auxiliary gas feed segment connected to the coupling segment and bent relative thereto in a direction having a component parallel to the direction in which the liquid evacuation duct extends in the vicinity of the coupling segment, and for the coupling segment to open out into the liquid evacuation duct via a section that is larger than the section of the feed segment, thus enabling any splashes of liquid to be trapped away from the gas feed segment.

In an embodiment of the invention, the auxiliary gas feed segment in the vicinity of the coupling segment is directed to feed the auxiliary gas in the same direction as the direction in which liquid is evacuated in the liquid evacuation duct.

In an embodiment of the invention that enables an extractor module to be obtained that is compact, the auxiliary gas admission duct forms a top extension of a bottom rectilinear segment of the duct forming the liquid evacuation duct, the auxiliary gas admission duct and the liquid evacuation duct being adjacent to the receptacle and opening out into it through a common fluid-passing window, a liquid deflector being provided above the fluid-passing window in the auxiliary gas admission duct.

In order to make the extractor module more compact, the receptacle, the auxiliary gas admission duct, the liquid evacuation duct, and the liquid inlet duct are constituted by a single piece.

An embodiment of the invention that is simple to implement makes provision for the means for preventing the auxiliary gas from passing into the liquid evacuation duct downstream from the common segment in the liquid-passing direction to comprise a siphon in the liquid evacuation duct.

In order to ensure that the siphon is compact, in an embodiment of the invention, it is made beneath the portion of the liquid evacuation duct that is coupled to the receptacle.

In order to make it possible where necessary to clean, inspect, or observe a portion of the liquid evacuation duct, provision is made in an embodiment of the invention for the liquid evacuation duct to include a passage leading to the outside above the level of the siphon and downstream therefrom in the liquid-passing direction.

An embodiment of the invention that makes it easier to collect the extracted gases and to deliver them to the gas receiving means, provision is made for the receptacle to comprise a body surmounted by a removable collar with the gas outlet duct being provided thereon. Naturally, this characteristic can be provided in any module for extracting gas samples of compounds present in an underground working liquid, and is independent of other characteristics.

In order to cause the liquid or the water to drop back into the receptacle, an embodiment of the invention makes provision for the gas outlet duct to open out into the bottom portion of the collar in contact with the inside of the body of the receptacle, making an angle that is inclined towards the inside of the body of the receptacle. Naturally, this characteristic can be provided in any module for extracting gas samples of compounds present in an underground working liquid, and is independent of other characteristics.

An embodiment of the invention makes provision for the gas outlet duct to comprise a first segment for coupling to the collar and which is extended beside the gas outlet by a segment of a section that is smaller than the smallest section of the coupling segment, so as to reduce the risk of underground working liquid passing to the analyzer module and detect the clogging of the outlet duct. Naturally, this characteristic can be provided in any module for extracting gas samples of compounds present in an underground working liquid and is independent of other characteristics.

In a second aspect; the invention provides an installation for analyzing gas samples, the installation including an extractor module as described above, in which the liquid inlet duct is connected to a module for taking underground working liquid and in which the gas outlet duct is coupled to an analyzer module for analyzing gas samples.

An embodiment of the invention requiring little expense makes provision for the auxiliary gas admission duct to communication with the atmosphere, and the gas-sample analyzer module includes gas suction means.

Another embodiment of the invention, enabling the extracted gas to be urged towards the gas outlet duct, makes provision for the auxiliary gas admission duct to be connected to a source of compressed auxiliary gas.

For more effective heating of the liquid contained in the receptacle, an embodiment of the invention that can be provided in any installation for analyzing gas samples and independent of other characteristics makes provision for a liquid heater module which is interposed, outside the extractor module, in the liquid circuit between the liquid taking module and the extractor module.

In order to reduce the risks of water reaching the gas sample analyzer module, provision is made in an embodiment of the invention that can be provided in any gas sample installation and that is independent of other characteristics, for the gas outlet duct to be connected to the gas-sample analyzer module via a water-trapping module.

An embodiment of the invention makes provision for the collar to be connected in a leaktight manner to the body of the receptacle via a support plate of the extractor module, which plate includes a passage between the inside of the body of the receptacle and the inside of the collar.

In an embodiment of the invention, the water-trapping module is provided with means for maintaining its temperature at a predetermined value.

An embodiment of the invention makes provision for the analyzer module to be connected to the water-trapping module via a gas duct comprising a first segment for coupling to the water-trapping module, extended beside the gas outlet by a second segment of an inside section smaller than the inside section of the coupling first segment. By means of this embodiment, the risk of the underground working liquid passing to the analyzer module and the risk of the gas outlet duct becoming blocked are reduced.

BRIEF DESCRIPTION OF THE DRAWINGS

The invention will be better understood after reading the following description made with reference to the accompanying drawings, given purely as non-limiting examples, and in which.

DETAILED DESCRIPTION OF THE INVENTION

Figure 1:
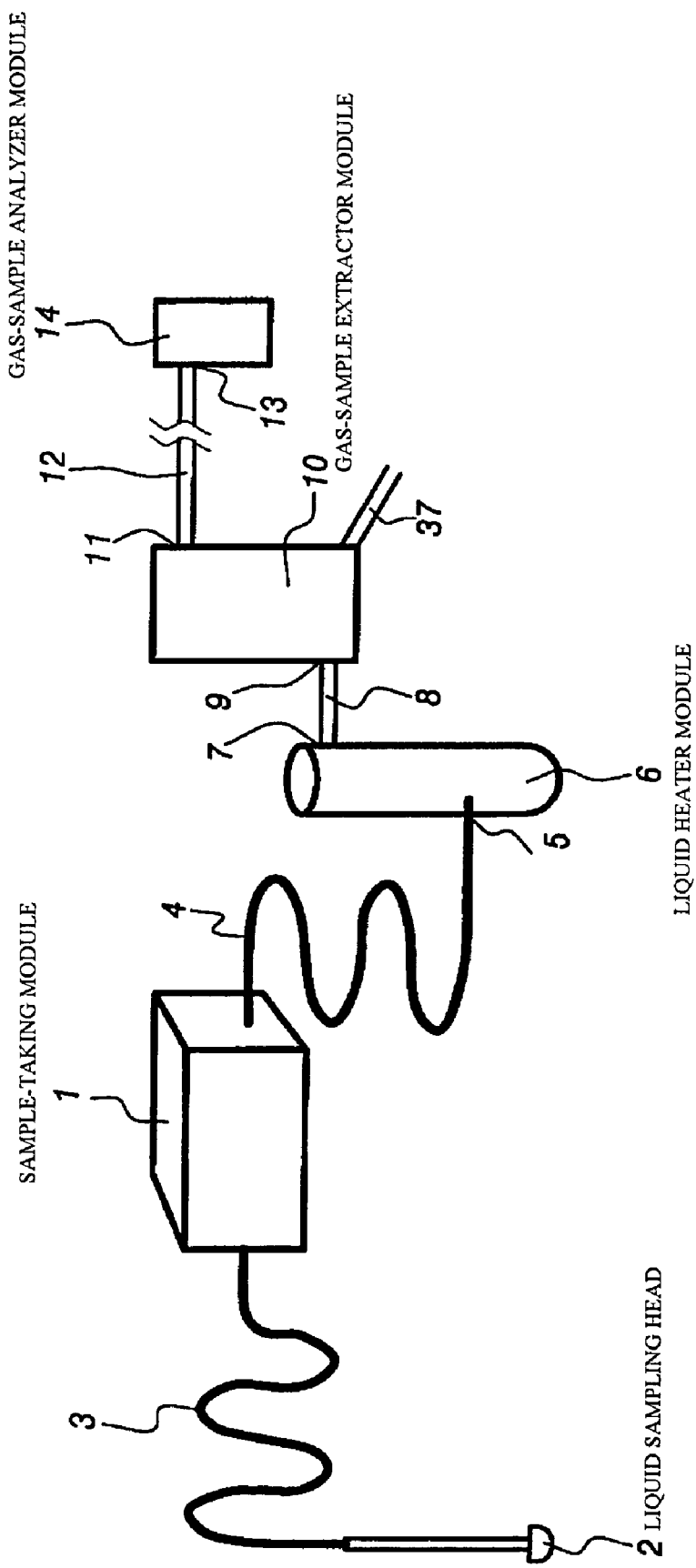
FIG. 1 is a diagram of an installation for analyzing samples of gas in accordance with the invention.

The invention is described below with reference to an installation for taking liquid that has come to the surface while drilling an oil well, thus constituting an underground working liquid, also referred to as an underground working fluid. Liquid in the form of mud is sent to the bottom of the well and is then raised by pumping, as is known to the person skilled in the art. The liquid that comes up to the surface is charged with gas and other substances present in the well, and that need to be extracted from the liquid that has come up to the surface in order to obtain information about the layers of ground through which the borehole passes, their composition, their richness, and their hydrocarbon content, and also about their drilling conditions. Naturally, the underground working liquid could equally well be any other liquid, such as, for example, water or oil raised from underground.

The extraction installation of the invention comprises a module for taking liquid from the borehole, e.g. comprising a motor-driven pump unit (not shown) enabling the liquid that comes from the well to be sucked in via a liquid-sampling head 2 or strainer which is pushed into the well, and a hose 3 for connection to the sample-taking module 1. The sample-taking module 1 sends the liquid that has been taken from the well via an outlet hose 4 to the inlet 5 of a liquid heater module 6. The sample-taking module 1 is constituted by a frame carrying a motor and gearbox unit with two outlets driving firstly a peristaltic pump for taking the liquid from the well via the hose 3 and the head 2 at a rate lying in the range 0.15 liters per minute ($\lambda$/min) to 0.5 $\lambda$/min and delivering it to the hose 4, and secondly a Bowden cable connected to the strainer 2 and driving a rotary scraper of the strainer, so as to prevent it from becoming clogged, as is described in U.S. Pat. No. 5,090,256.

By way of example, the liquid heater module 6 includes a heating resistance element (not shown) that is powered electrically. The inlet 5 for liquid entering the module 6 is located in the bottom thereof, while the outlet 7 for liquid leaving the module 6 is in the top thereof. By way of example, the power rating of the module 6 may lie in the range 1 kilowatt (kW) to 3 kW, thus enabling the liquid that goes from its inlet 5 to the outlet 7 to be raised to a selected temperature lying in the range 25° C. to 120° C., for example, and typically lying in the range 60° C. to 90° C. The working volume of the module 6 lies, for example, in the range 0.5 liters ($\lambda$) to 2.5 $\lambda$. The outlet 7 for liquid leaving the module 6 is connected via a hose 8 to the inlet duct 9 for liquid entering the gas-sample extractor module 10 of the invention. The heater module 6 is separate from the extractor module 10. The module 10 has a gas outlet duct 11 connected via a gas outlet hose 12 to an inlet access 13 of a gas-sample analyzer module 14.

Figure 2:
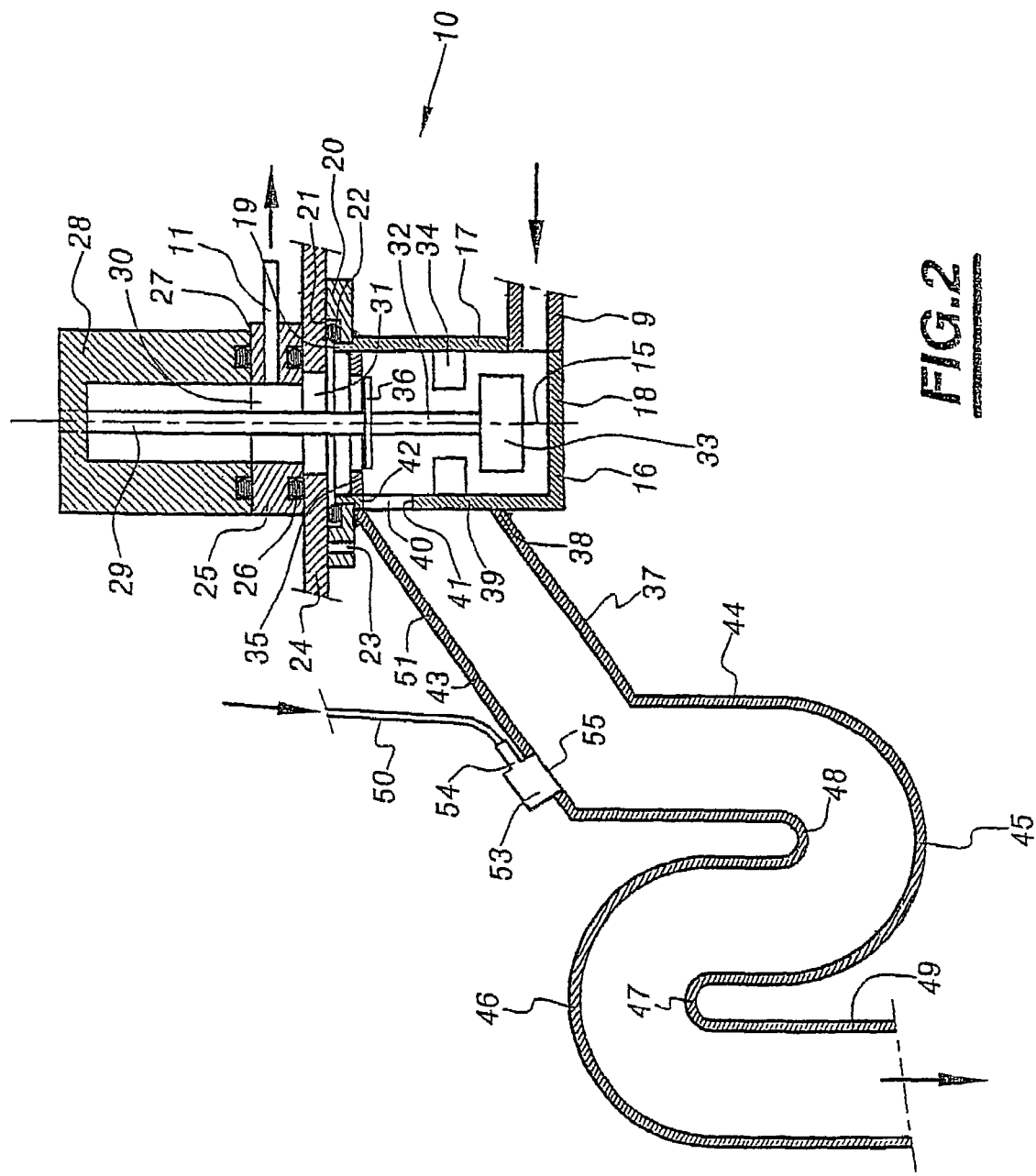
FIG. 2 is a diagrammatic vertical section of a first embodiment of the extractor module in accordance with the invention.

In FIG. 2, the extractor module 10 of the invention comprises a receptacle 16, for example a receptacle having a body in the form of a circular cylinder about an axis 15 of symmetry. Naturally, any other geometrical shape for the body of the receptacle 16 could be provided. In the description below, the axis of symmetry 15 of the receptacle 16 is assumed to be vertical. The liquid inlet duct 9 opens out into the receptacle 16 in the bottom portion thereof, for example and as shown, into the bottom of the cylindrical side surface 17 of the receptacle 16. In embodiments that are not shown, the liquid inlet duct 9 opens out into the bottom 18 of the receptacle 16. A washer 20 is supported by the upper portion 19 of receptacle 16. The washer 20 has a circular recess to receive an O-ring gasket 22. The washer also has a through-hole 23 to allow a fastener (not shown) to secure the washer 20 to a receptacle support plate 24. Upper portion 19 of the receptacle 16 is held to face the support plate 24 in a leaktight manner by the O-ring 22.

Beside the plate 24 of the support, at a distance from the edge 19, there is provided a removable collar 25 held by any suitable means against the plate 24, and in leaktight manner, by a sealing O-ring 26. The collar 25 has a top surface 27 on which there is fixed an electric motor 28 whose central rotor 29 passes through central recesses 30, 31 allowing gas to pass through and provided respectively within the collar 25 and the support plate 24. The gas outlet duct 11 communicates with the recess 30 within the collar 25. The shaft 29 is connected inside the receptacle 16 to a rotary stirrer 32, e.g. formed by a rod extending the shaft 29 and having one or more blades 33 fixed thereto and dipping into the receptacle 16. The shaft 29 and the stirrer rod extend along the axis 15 of the receptacle 16, for example, and the blades 33 are radial relative to the axis 15, for example, and there are four of them, or two as shown. One or more liquid deflectors 34, e.g. provided in the form of vertical plates, are fixed inside the side wall 17 above the level of the blades 33 so as to create turbulence inside the receptacle 16 due to the liquid therein rotating. A washer 35 is fixed inside the side surface 17 close to the edge 19 to protect the top of the receptacle 16 against splashes of liquid due to the stirring. A protective washer 36 is also fixed to the shaft 29 slightly beneath the washer 35, the protective washer 36 having an outside diameter that is smaller than the inside diameter of the washer 35 so as to enable the shaft 29 to be inserted in the receptacle 16. Naturally, the protective washer 36 could equally well be situated at the same level as or above the washer 35.

An external duct 37 for evacuating liquid from the receptacle 16 is fixed to the side surface 17 of the receptacle 16 via a connection portion 38 between them. The connection portion 38 defines a portion 39 of the side surface 17 in which there is provided a fluid-passing window 40 for passing liquid and gas. The window 40 is provided above the blades 33 of the stirrer 32 and the deflectors 34, and beneath the inside washer 35. The fluid-passing window 40 has a bottom edge 41 and a top edge 42. The bottom edge 41 is at a distance from the connection portion 38.

Figure 4:
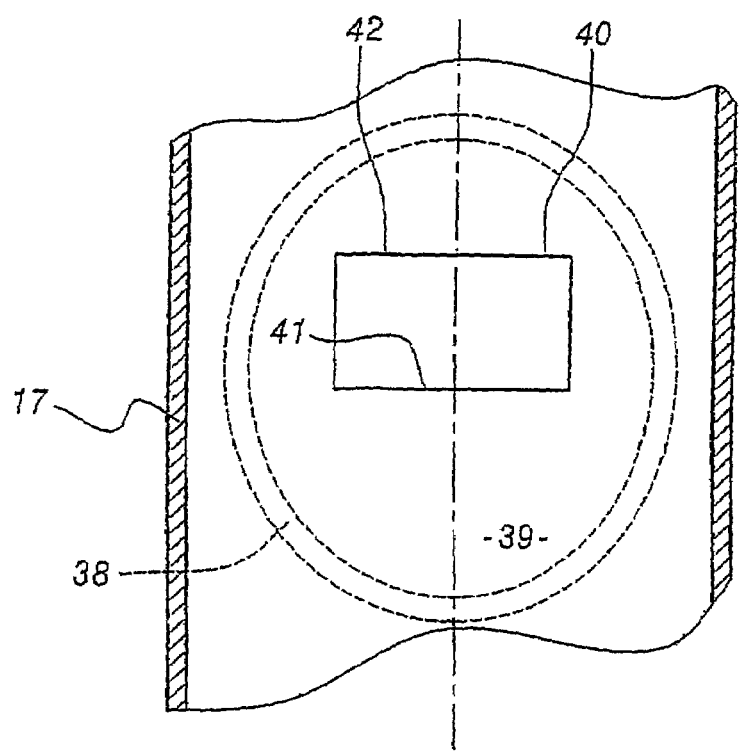
FIG. 4 is a diagram of an inside portion of the extractor module of FIGS. 2 and 3, including a fluid-passing window.

As shown in FIG. 4, the bottom edge 41 lies in a plane perpendicular to the axis of symmetry 15 of the cylindrical side surface 17 of the receptacle 16, as does the top edge 42. By way of example, the window is rectangular. In embodiments that are not shown, the bottom edge 41 and/or the top edge 42 are contained in part only in such a plane. The stirrer 32 is controlled in such a manner as to cause the liquid to rise above the bottom edge 41 so that the liquid passes into the duct 37. The plane portion of the bottom edge 41, or the entire bottom edge when it occupies a plane as shown, ensures to a large extent that the window 40 does not become blocked by the liquid. By way of example, the window 40 may have a through section of area lying in the range 1 square centimeter ($cm^2$) to 6 $cm^2$.

The external liquid extraction duct 37 has a rectilinear segment 43 for extracting liquid from the receptacle 16, connected firstly to the connection portion 38 and secondly to a vertical segment 44 for coupling and downward extension. The liquid outlet segment 43 slopes downwards, e.g. at an angle lying in the range 25° to 45° relative to the axis 15. The extension segment 44 is downwardly connected to an S-shaped segment 45 having two bends, with an upward first bend 45 and a downward second bend 46. The bottom portion 47 of the downward second bend 46 is at a level that is higher than the top portion 48 of the upward first bend 45, thus implementing a siphon for the liquid. The bottom portion 47 of the second bend is also below the liquid outlet segment 43. The downward second bend 46 is connected at its bottom end to a segment 49 for evacuating liquid externally, e.g. by gravity into a waste vessel or the like (not shown). Thus, when liquid fills the upward first bend 45 from the top portion 48 of said first bend 45, gas coming from the extension segment 44 is prevented from passing towards the downward second bend 46, and any gas coming from the liquid evacuation segment 49 is prevented from passing towards the extension segment 44. The segments 43, 44, and 49, and the bends 45 and 46 may be circularly cylindrical, for example. Naturally, any other means could be provided for making the segments connected to the extension segment 44 gastight.

A duct 50 for introducing an auxiliary gas is connected to the liquid outlet segment 43 of the receptacle 16 between the extension segment 44 and the connection portion 38 of the receptacle 16. The auxiliary gas may be air, or any inert gas, such as nitrogen, for example.

The dimensions of the extractor module 10 can be as follows, for example. The liquid outlet segment 43 has a diameter lying in the range 15 millimeters (mm) to 55 mm and a length lying in the range 50 mm to 150 mm. The volume of the receptacle 16 lies in the range 40 cubic centimeters ($cm^3$) to 300 $cm^3$, and the liquid reaches the liquid inlet duct 9 at a rate lying in the range 0.15 λ/min to 0.5 λ/min. The speed of rotation of the stirrer lies in the range 1500 revolutions per minute (rpm) to 3500 rpm. By way of example, the auxiliary gas admission duct 50 has a diameter lying in the range 2 mm to 6 mm, and is at a distance lying in the range 40 mm to 140 mm from the connection portion 38, and possesses an angle of inclination lying in the range 30° to 50° relative to the axis 15 of the receptacle 16, for example.

When the stirrer 32 is put into operation, the liquid introduced via the inlet duct 9 is stirred in the receptacle 16 and sent into the liquid evacuation duct 37 by passing through the window 40. The liquid sent into the liquid evacuation duct 37 moves down the liquid outlet segment 43, and then along the extension segment 44, the first bend 45, and once its level exceeds the bottom portion 47 of the second bend 46, it moves down the liquid evacuation segment 49. Because of the stirring of the liquid in the receptacle 16, gas is extracted from the liquid. The auxiliary gas introduced via the introduction duct 50 is prevented from leaving the extension segment 44 because of the gas seal means provided downstream therefrom, so it is sent into the liquid outlet segment 43, through the window 40, into the receptacle 16 and through the washer 35, the recess 31, and the recess 30 so as to leave via the outlet duct 11. Thus, the auxiliary gas serves to entrain the gas or gases extracted from the liquid. In FIG. 2, a duct for admitting auxiliary gas into the receptacle 16 is formed by the auxiliary gas introduction duct 50 and by the portion of the liquid outlet segment 43 that lies between the outlet of the auxiliary gas introduction duct 50 into the liquid outlet duct 43 and the connection portion 38. There exists a common segment 51 constituted in FIG. 2 by the portion of the liquid outlet segment 43 that extends between the connection portion 38 and the outlet of the auxiliary gas introduction duct 50 into the liquid outlet duct 43, which has liquid flowing through it in one direction and auxiliary gas in the opposite direction, thereby likewise encouraging the extraction of gas from the liquid. Thus, the auxiliary gas flow circuit and the liquid flow circuit present a common segment outside the receptacle 16. The auxiliary gas introduction duct 50 is coupled to a source of compressed auxiliary gas for allowing the gas extracted from the liquid to be transferred towards the gas outlet duct 11. In a variant, the auxiliary gas introduction duct 50 is connected to the atmosphere and the gas-sample analyzer module 14 has a pump or other means for sucking in auxiliary gas together with the gas extracted from the liquid.

Figure 3:
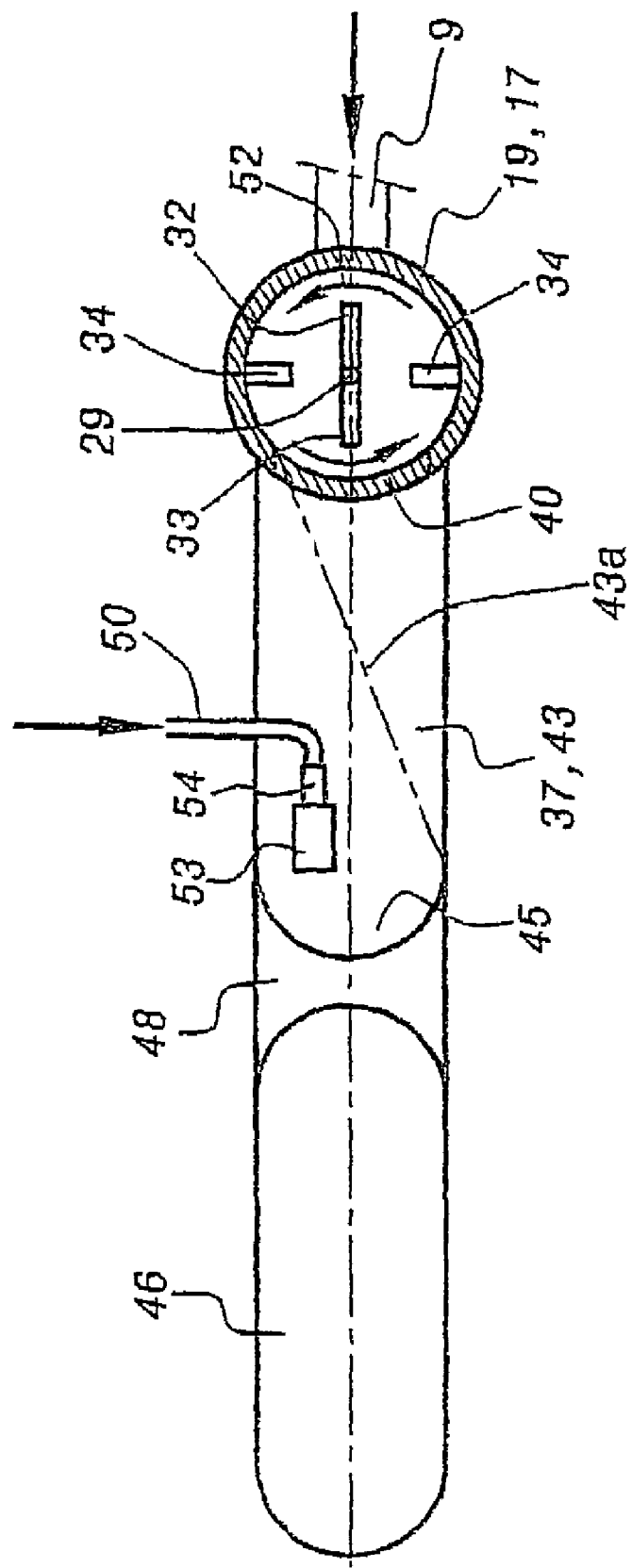
FIG. 3 is a diagrammatic plan view of the FIG. 2 extractor module.

In FIGS. 2 and 3, the auxiliary gas introduction 50 opens out into the liquid outlet segment 43 in the bottom portion thereof, close to the connection segment 44. In FIG. 3, it can be seen that the auxiliary gas introduction duct 50 opens out into the liquid outlet segment 43 at a portion thereof that is situated further upstream than downstream in the direction 52 of rotation of the blades 33 of the stirrer 32. The auxiliary gas introduction duct 50 has a segment 53 for coupling to the liquid outlet segment 43 and an auxiliary gas feed segment 54 coupled to said segment 53. The segment 54 is bent relative to the segment 53 to extend parallel to the direction in which the liquid outlet duct 43 extends and to extend upwards, so that the auxiliary gas penetrates into the feed segment 54 in the same direction as the direction in which liquid flows in the liquid outlet segment 43. The section 55 allowing the auxiliary gas to pass from the coupling segment 53 is greater than that of the feed segment 54. This disposition shelters the segment 54 from any splashing by the liquid present in the liquid outlet segment 43 to the right-hand side of the chain-dotted line 43a which represents the limiting trajectory for such splashing.

Figure 5:
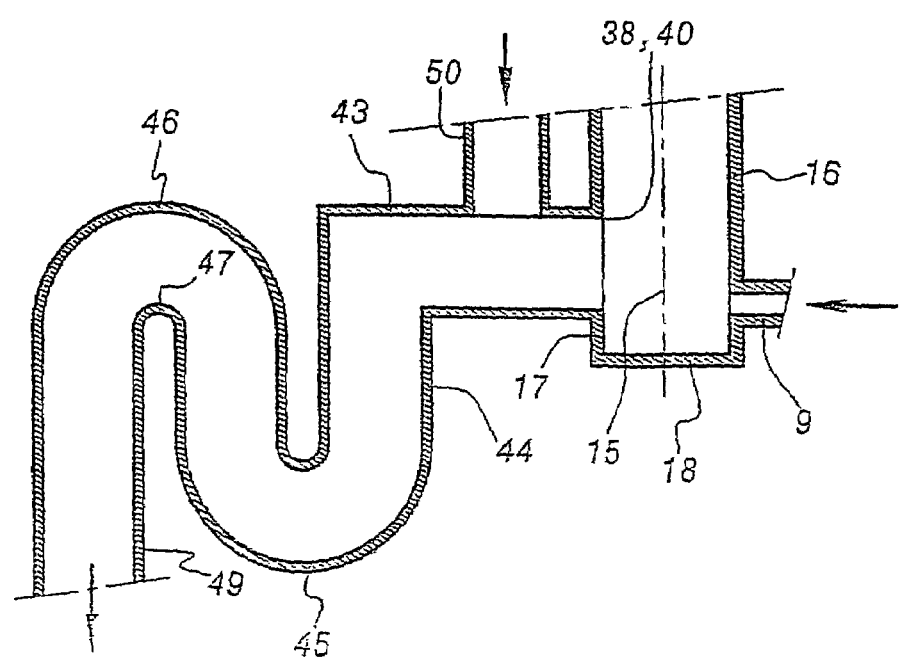
FIG. 5 is a diagrammatic vertical section showing a second embodiment of the extractor module in accordance with the invention.
Figure 6:
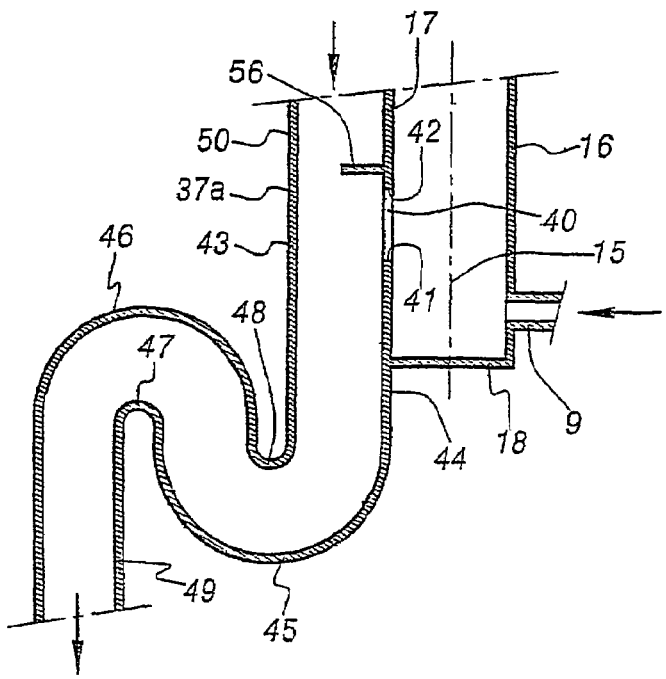
FIG. 6 is a diagrammatic vertical section showing a third embodiment of the extractor module in accordance with the invention.
Figure 7:
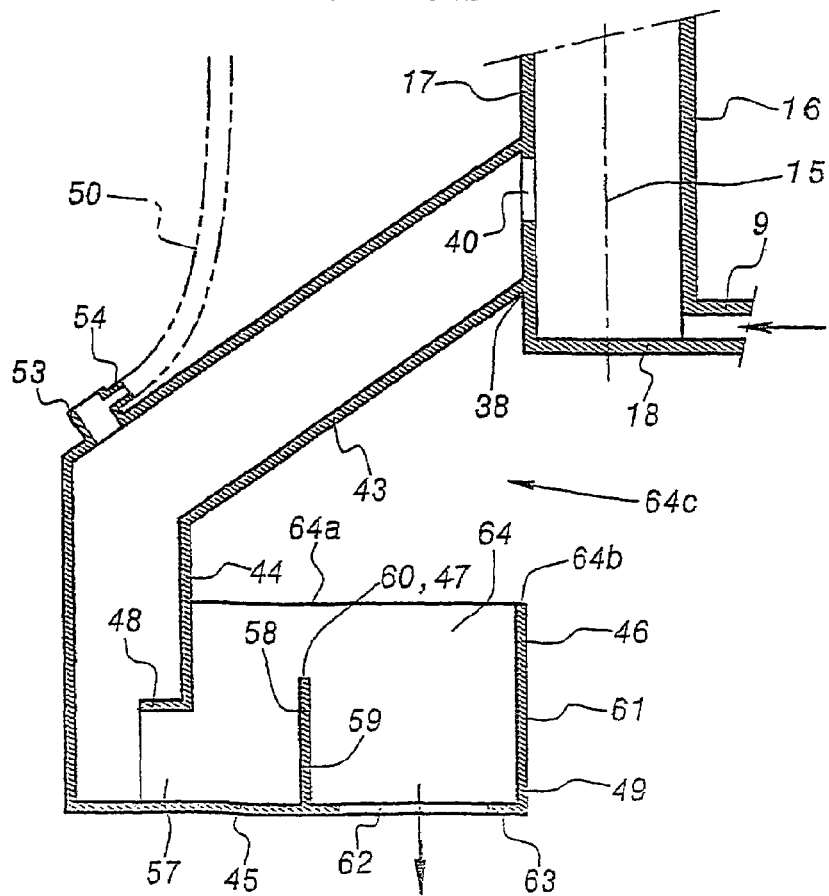
FIG. 7 is a diagrammatic vertical section showing a fourth embodiment of the extractor module in accordance with the invention.

In FIGS. 5, 6, and 7, the stirrer 32, the rotor 29, and the portions situated above the receptacle 16 are not shown for reasons of clarity. Naturally these portions should be present in the same manner to enable the extractor module to operate. The description below relates to those portions which differ for FIGS. 1 to 4.

In the embodiment shown in FIG. 5, the liquid outlet segment 43 is substantially horizontal and opens out fully firstly into the side surface 17 of the receptacle 16 and secondly into the coupling segment 44. The auxiliary gas introduction duct 50 opens out into the liquid outlet segment 43 in a top portion thereof between the coupling segment 44 and the portion 38 for connection to the receptacle 16. The fluid-passing window 40 is formed by the connection portion 38, for example.

In the embodiment shown in FIG. 6, a duct 37a is adjacent to the side surface 17 of the receptacle 16, is vertical, and communicates with the inside of the receptacle 16 via the fluid-passing window 40. The portion of duct 37a situated beneath the top edge 42 of the window 40 forms the liquid outlet segment 43 of the receptacle 16 and the coupling segment 44, while the portion of duct 37a situated above the bottom edge 41 of the window 40 forms the auxiliary gas admission and introduction duct 50. A deflector 56 is provided in the duct 37a above and close to the top edge 42 of the window 40 so as to deflect downwards any splashes of liquid coming from the receptacle 16. The common segment between the liquid outlet duct and the auxiliary gas admission duct 50 is formed by the portion of the duct 37a that is adjacent to the fluid-passing window 40.

In the embodiment shown in FIG. 7, the auxiliary gas introduction duct 50, the liquid outlet segment 43, the coupling segment 44, and the receptacle 16 are analogous to the embodiments shown in FIGS. 2 to 4. The first bend 45 comprises a rectilinear segment 57 forming the top portion 48 of the upward first bend 45 and coupled firstly at right angles to the coupling segment 44 and secondly at right angles to an upward liquid outlet segment 58 having a vertical wall 59 fixed to the segment 57 at a distance from the coupling segment 44. The top edge 60 of the wall 59 forms the bottom portion 47 of the second bend 46. A wall 61 is connected to the wall 59 to form the liquid evacuation segment 49, a liquid outlet window 62 being provided in the bottom portion 63 coupling the wall 61 to the wall 59. The first bend 45 and the second bend 46 as formed in this way, the wall 59, and the wall 61 all lie beneath the liquid outlet segment 43, a portion of the wall 61 being vertically in alignment with a generator line of the connection portion 38 of the side surface 17 of the receptacle 16. The wall 61 joins the coupling segment 44 via a peripheral wall 64 surrounding the wall 59 and having a top edge 64a that is higher than the edge 60. The top edge 64b of the wall 61 is at a distance from the bottom 18 of the receptacle 16 and at a distance from the liquid outlet segment 43, thereby defining a passage 64c leading to the outside, making it possible, where necessary, to insert a cleaning tool. In addition, this embodiment makes it possible to obtain an extractor module having a structure that is compact and in a single piece.

Figure 8:
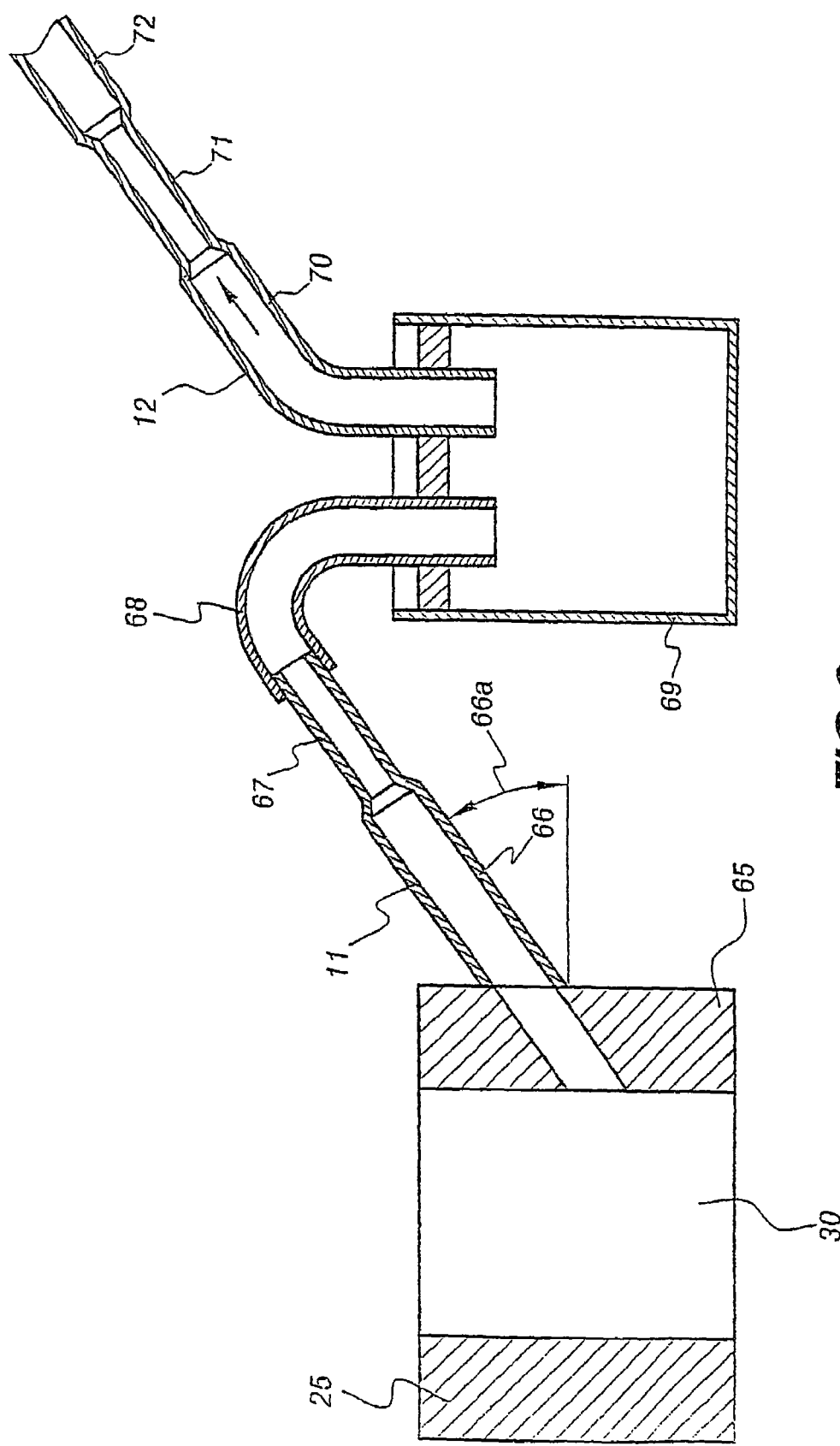
FIG. 8 is a diagrammatic vertical section of a collar forming part of the extractor module in accordance with the invention.

In FIG. 8, the gas outlet duct 11 passes through the side wall 65 of the collar 25 and is extended outwards as a segment 66 coupled to the collar 25 and slopes upwards at a determined angle 66a. The coupling segment 66 is circularly cylindrical, for example, having a diameter lying in the range 2 mm to 10 mm. The coupling segment 66 is connected at its end remote from the collar 25 to a segment 67 of inside cross-section that is smaller than that of the coupling segment 66. A hose 68 of inside cross-section greater than that of the segment 67 is coupled to, and for example surrounds, the free end of the segment 67, and plunges into a receptacle 69 for trapping the water contained in the incoming gas. The gases leave the water-trapping receptacle 69 via the gas outlet duct 12 which is connected to the gas-analyzer module 14. The gas duct 12 has a first segment 70 coupled to the water-trapping module 69, the segment 70 being extended towards the gas outlet by a second segment 71 of inside section smaller than that of the coupling segment 70, and in turn coupled to the analyzer module 14 via a third segment 72 of the gas duct, of section greater than that of the segment 71.

The invention thus makes it possible, with good efficiency, to extract the gas contained in the liquid that is introduced into the extractor module, making it particularly suitable for use in continuous analysis of gas brought to the surface while drilling a borehole.

The invention claimed is:

1. An extractor module for extracting samples in gas phase of compounds present in an underground working liquid, the extractor module comprising:
    a receptacle for said liquid, associated with means for stirring the liquid in the receptacle in order to extract the compounds in the gas phase from the liquid, and connected to the receptacle when it is operating to extract gas;
    at least one liquid inlet duct for admitting liquid into the receptacle;
    at least one liquid evacuation duct for evacuating liquid from the receptacle;
    at least one auxiliary gas admission duct for admitting auxiliary gas into the receptacle; and
    at least one outlet duct for delivering auxiliary gas and gas extracted from the liquid, for connection to gas reception means,
    wherein the auxiliary gas admission duct and the liquid evacuation duct include at least one common segment for passing the liquid and the auxiliary gas, means for preventing the auxiliary gas from passing being provided in the liquid evacuation duct downstream from said common segment in the liquid-passing direction.

2. An extractor module according to claim 1, wherein the auxiliary gas admission duct opens out into the liquid evacuation duct in a portion lying at a distance from the receptacle.

3. An extractor module according to claim 1, wherein the liquid evacuation duct slopes downwards relative to the receptacle.

4. An extractor module according to claim 1, wherein the auxiliary gas admission duct forms a top extension of a bottom rectilinear segment of the duct forming the liquid evacuation duct, the auxiliary gas admission duct and the liquid evacuation duct being adjacent to the receptacle and opening out into it through a common fluid-passing window, a liquid deflector being provided above the fluid-passing window in the auxiliary gas admission duct.

5. An extractor module according to claim 1, wherein the receptacle, the auxiliary gas admission duct, the liquid evacuation duct, and the liquid inlet duct are constituted by a single piece.

6. An extractor module according to claim 1, wherein the common segment communicates with the receptacle via a fluid-passing window for passing the auxiliary gas and the liquid, and having, in its bottom portion, at least one edge lying substantially in a plane.

7. An extractor module according to claim 6, wherein the fluid-passing window has a rectangular profile.

8. An extractor module according to claim 1, wherein the auxiliary gas admission duct opens out into the liquid evacuation duct at a portion that is situated so as to be substantially sheltered from splashes of liquid coming from the receptacle.

9. An extractor module according to claim 8, wherein the stirring means comprise a rotary stirrer and the auxiliary gas admission duct opens out into the liquid evacuation duct at a portion situated further upstream than downstream in the direction of rotation of the rotary stirrer.

10. An extractor module according to claim 1, wherein the auxiliary gas admission duct presents a segment for coupling to the liquid evacuation duct and an auxiliary gas feed segment connected to the coupling segment and bent relative thereto in a direction having a component parallel to the direction in which the liquid evacuation duct extends in the vicinity of the coupling segment, and the coupling segment opens out into the liquid evacuation duct via a section that is larger than the section of the feed segment.

11. An extractor module according to claim 10, wherein the auxiliary gas feed segment in the vicinity of the coupling segment is directed in the same direction as the direction in which liquid is evacuated in the liquid evacuation duct.

12. An extractor module according to claim 1, wherein the means for preventing the auxiliary gas from passing into the liquid evacuation duct downstream from the common segment in the liquid-passing direction comprise a siphon in the liquid evacuation duct.

13. An extractor module according to claim 12, wherein the siphon is made beneath the portion of the liquid duct that is coupled to the receptacle.

14. An extractor module according to claim 12, wherein the liquid evacuation duct includes a passage leading to the outside above the level of the siphon and downstream therefrom in the liquid-passing direction.

15. An extractor module according to claim 1, wherein the receptacle comprises a body surmounted by a removable collar on which the gas outlet duct is provided.

16. An extractor module according to claim 15, wherein the gas outlet duct opens out into the bottom portion of the collar in contact with the inside of the body of the receptacle, making an angle that is inclined towards the inside of the body of the receptacle.

17. An extractor module according to claim 15, wherein the gas outlet duct comprises a first segment for coupling to the collar and extended beside the gas outlet by a segment of section that is smaller than the smallest section of the coupling segment.

18. An installation for analyzing gas samples, the installation comprising an extractor module according to claim 1, in which the liquid inlet duct is connected to a module for taking underground working liquid and in which the gas outlet duct is coupled to an analyzer module for analyzing gas samples.

19. An installation according to claim 18, wherein the auxiliary gas admission duct communicates with the atmosphere, and the gas-sample analyzer module includes gas suction means.

20. An installation according to claim 18, wherein the auxiliary gas admission duct is connected to a source of compressed auxiliary gas.

21. An installation according to claim 18, wherein a liquid heater module is interposed in the liquid circuit, outside the extractor module, between the liquid-taking module and the extractor module.

22. An installation according to claim 18, wherein the receptacle comprises a body surmounted by a removable collar on which the gas outlet duct is provided, and wherein the collar is connected in leaktight manner to the receptacle via an extractor module support plate, which support plate includes a passage between the inside of the body of the receptacle and the inside of the collar.

23. An installation according to claim 18, wherein the gas outlet duct is connected to the gas-sample analyzer module via a water-trapping module.

24. An installation according to claim 23, wherein the water-trapping module is provided with means for maintaining its temperature at a predetermined value.

25. An installation according to claim 23, wherein the analyzer module is connected to the water-trapping module via a gas duct comprising a first segment for coupling to the water-trapping module, extended beside the gas outlet by a second segment of inside section smaller than the inside section of the coupling first segment.

* * * * *